(12) United States Patent
Sliwinski et al.

(10) Patent No.: US 8,372,442 B2
(45) Date of Patent: Feb. 12, 2013

(54) LIQUID NUTRITIONAL COMPOSITION FOR BARIATRIC SURGERY PATIENTS

(75) Inventors: Edward Lucian Sliwinski, Oss (NL); Marcel Minor, Wageningen (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 12/966,243

(22) Filed: Dec. 13, 2010

(65) Prior Publication Data

US 2011/0081424 A1 Apr. 7, 2011

Related U.S. Application Data

(63) Continuation of application No. PCT/EP2009/004468, filed on Jun. 19, 2009.

(30) Foreign Application Priority Data

Jun. 19, 2008 (WO) .................. PCT/EP2008/004938

(51) Int. Cl.
*A01N 59/16* (2006.01)
(52) U.S. Cl. ....................................................... 424/646
(58) Field of Classification Search .................. 424/646
See application file for complete search history.

(56) References Cited

U.S. PATENT DOCUMENTS

2008/0107715 A1 5/2008 Miller

FOREIGN PATENT DOCUMENTS

| WO | WO 99/53777 | 10/1999 |
|---|---|---|
| WO | WO 00/21391 | 4/2000 |
| WO | WO 02/052954 | 7/2002 |
| WO | WO 2004/017764 | 3/2004 |
| WO | WO 2007/069900 | 6/2007 |

OTHER PUBLICATIONS

"Optisource® High Protein Drink," 2007.*
Folope et al., Carences nutritionnelles liées á la chirugie de l' obésité, Gastroenterol Clin Biol 31: 369-377 (2007).*
Roberfroid, Concepts in Functional Foods: The Case of Inulin and Oligofructose, J Nutr 129: 1398S-1401S (1999).*
Howard et al. Sugar and Cardiovascular Disease: A Statement for Healthcare Professionals from the Committee on Nutrition of the Council on Nutrition, Physical Activity, and Metabollism of the American Heart Association, Circulation 106: 523-527 (2002).*
Thorsdottir et al., Randomized trial of weight-loss-diets for young adults varying in fish and fish oil content, Int J Obesity 31: 1560-1566 (2007), published online May 15, 2007.*
Brighenti F, Casiraghi MC, Canzi E, Ferrari A. Effect of consumption of a ready-to-eat breakfast cereal containing inulin on the intestinal milieu and blood lipids in healthy male volunteers. Eur J Clin Nutr 1999; 53:726-33.
Buchwald H. et al. Bariatric Surgery: A systematic review and analysis. JAMA Oct. 13, 2004 vol. 292 No. 14 pp. 1724-1737.
Cook JD, Monsen ER. Vitamin C, the common cold, and iron absorption. Am J Clin Nutr 1977; 30:235-41.
International Search Report for PCT/EP2009/004468 dated Mar. 8, 2010.
International Search Report for PCT/EP2009/004469 dated Oct. 27, 2009.
Jackson KG, Taylor GR, Clohessy AM, Williams CM. The effect of the daily intake of inulin on fasting lipid, insulin and glucose concentrations in middle-aged men and women. Br J Nutr 1999; 82:23-30.
Malinowski SS. Nutritional and metabolic complications of bariatric surgery. Am J Med Sci 2006; 331:219-25.
Parkes E. Nutritional management of patients after bariatric surgery. Am J Med Sci 2006; 331:207-13.
Poitou et al., carences nutritionelles apres bypass gastriquie: diagnostic, prevention et traitement, Chaiers de Nutrition et de Dietetique, vol. 42, No. 3, Jun. 2007, pp. 153-165, XP008102601.
Tucker et al., Nutritional consequences of weight-loss surgery, Medical Clinics of North America, W.B. Saunders Company, Philadelphia US, vol. 91, No. 3, May 1, 2007, pp. 499-514 XP008101698.
www.bariatricchoice.com, Champion Nutrition Low carb UltraMet, May 14, 2008, pp. 1-3, XP002567239.
www.bariatricchoice.com; Chocolite Sugar-Free Protein Shake Mix, May 14, 2008, pp. 1-3 XP002567238, Bariatric Choice—The leading Source of Nutrition for Bariatric Patientss.
www.healthsuperstore.com, Champion Nutrition Low Carb Ultramet Chocolate, May 14, 2008, pp. 1-4, XP002567409.
www.lowcabchocolates.com; Health Smart Foods—Chocolite (Formerly Lean-up) Protein Shake Mix, Apr. 21, 2008, pp. 1-3 XP002567408.
Xanthakos SA, Inge TH. Nutritional consequences of bariatric surgery. Curr Opin Clin Nutr Metab Care 2006; 9:489-496.

* cited by examiner

*Primary Examiner* — Robert T Crow
*Assistant Examiner* — Thor Nielsen
(74) *Attorney, Agent, or Firm* — Woodard, Emhardt, Moriarty, McNett & Henry LLP

(57) ABSTRACT

A ready-to-consume liquid nutritional composition which is particularly suitable for use by morbidly obese patients pre- and post-bariatric surgery. The composition comprises an energy content between 80-160 kcal/100 ml, a protein content between 40-80 En %, a digestible carbohydrate content between 0-30 En %, a fat content between 5-40 En %, a soluble dietary fiber content between 1.5-8 g/100 kcal, and micronutrients. The micronutrients comprise calcium in an amount between 150-1000 mg/100 kcal, phosphorus in an amount between 100-1000 mg/100 kcal, with a Ca:P ratio of at least 1.0, iron in an amount between 4-50 mg/100 kcal, vitamin D in an amount between 2-400 mcg/100 kcal and vitamin B12 in an amount between 0.5-300 mcg/100 kcal.

25 Claims, No Drawings

LIQUID NUTRITIONAL COMPOSITION FOR BARIATRIC SURGERY PATIENTS

CROSS REFERENCE TO RELATED APPLICATIONS

This application is a continuation of PCT/EP2009/004468 FILED Jun. 19, 2009, which claims the benefit of PCT/EP2008/004938 filed Jun. 19, 2008.

FIELD OF THE INVENTION

The invention relates to ready-to-consume liquid nutritional compositions particularly suitable for use by morbidly obese patients pre and post bariatric surgery. The product helps to decrease liver size when used in patients following a calorie restricted diet in the period preceding bariatric surgery and further helps to maintain optimal nutritional requirements in the post bariatric surgery patients.

The composition comprises protein, digestible carbohydrate, fat, dietary fiber and micronutrients. Preferably the composition is high in protein and low in calories, and has neutral pH. It is also preferred that the composition is highly concentrated and thus can be offered in relatively small dosages. The composition may optionally be nutritionally complete.

BACKGROUND OF THE INVENTION

The rate of increase in obesity in the Western world is a major health problem affecting millions of people. Bariatric surgical procedures represent a successful way to achieve significant weight reduction in morbidly obese individuals. Following surgery it is estimated that up to one-third of the patients suffer nutritional deficiencies that cannot be corrected by normal diet alone.

From the literature, it is evident that nutritional deficiencies are common in both pre and post bariatric surgery patients. These deficiencies are specific depending on the type of surgery performed and post-operative deficiencies are further exacerbated. In the US the most common gastric bypass procedure is Roux-en-Y gastric bypass (RYGBP), which reduces the size of the stomach using surgical staples to cause restriction [1]. Then, the stomach is reattached to the jejunum, bypassing the duodenum and causing malabsorption. Two other less often performed types of bariatric surgery are: Tube gastrectomy or gastroplasty (TG) and Bilio-pancreatic diversion (BPD). Outside the US, laparoscopic gastric banding (LAGB) is the preferred type of bariatric surgery. In this procedure, a hollow band of special material is placed around the stomach near its upper end, creating a small pouch and a narrow passage into the larger remainder of the stomach.

TG and LAGB are purely restrictive, resulting in a 30-50 ml gastric pouch. Normal absorption is still possible, but deficiencies occur as a result of the greatly reduced overall volume of food intake. RYGBP is predominantly restrictive but also results in mild fat and protein malabsorption. The BPD is a primarily malabsorptive procedure with some restrictions [2,3]. Post surgery patients only are able to eat small portions at the time. To avoid shortages it is therefore crucial that the food offered to them is highly concentrated.

Large liver size impedes laparoscopic surgery in this patient group. An intense pre-surgery weight loss programme (4-6 weeks) has been found to significantly reduce liver size. Currently available weight loss products are not designed to address specific micronutrient needs of this patient group without additional multivitamin supplementation as they only contain micronutrients up to RDA levels. To meet RDAs for micronutrients, up to 5 servings of a protein containing weight management formula may need to be consumed in addition to multivitamins taken several times a day. The need to take several supplements each day can lead to reduced compliance over time resulting in clinical deficiencies.

Protein malnutrition is a real risk in bariatric surgery patients. Many patients require protein supplementation during the early phases of rapid weight loss, to prevent excessive loss of muscle mass. The advantage of a high protein, low calorie product specifically designed to meet or exceed micro-nutrient requirements, for use in patients pre and post bariatric surgery, is that patients can learn to combine healthy eating and product use without total reliance on meal replacers even before the surgical procedure is performed.

PRIOR ART

The commercially available product FORTIMEL® is a relatively low calorie, high protein product (1 kcal/ml), based on milk proteins as protein source, comprising 10 g/100 ml of proteins (40 En %), 2.1 g/100 ml of fat (19 En %), and 10.3 g/100 ml of digestible carbohydrates (41 En %), and is provided in a 200 ml unit dosage. This product has a relatively low protein level compared to the invention and does not contain dietary fiber and EPA+DHA. The carbohydrate source is maltodextrin which is a simple sugar and in the current dose might be disadvantageous regarding late gastric dumping. Furthermore the product is not highly concentrated. A dosage of 200 ml is required to supply the patient with 20 g protein. It is of crucial importance for post bariatric surgery that the nutrients can be offered in a small volume of 150 ml, preferably 125 ml.

The commercially available product CARNATION® INSTANT BREAKFAST® NO SUGAR ADDED is a relatively low calorie, high protein product (0.48 kcal/ml), based on milk proteins as protein source, comprising 3.8 g/100 ml of proteins (32 En %), 1.6 g/100 ml of fat (28 En %) and 4.8 g/100 ml of digestible carbohydrates (40 En %), and is provided in a 315 ml unit dosage. This product has a low protein level compared to the invention and does not contain dietary fiber and EPA+DHA. The carbohydrate source is maltodextrin which is a simple sugar and in the current dose might be disadvantageous regarding late gastric dumping. Furthermore the product is not highly concentrated. A dosage of >500 ml is required to supply the patient with 20 g protein. It is of crucial importance for post bariatric surgery that the nutrients can be offered in a small volume of 150 ml, preferably 125 ml.

The commercially available product OPTISOURCE® High Protein Drink is a relatively low volume, high protein product (0.85 kcal/ml), based on milk protein as protein source, comprising 10.2 g/100 ml of proteins (48 En %), 2.5 g/100 ml of fat (27 En %), and 5.1 g/100 ml of digestible carbohydrates (24 En %), and is provided in a 118 ml unit dosage. This product does not contain dietary fiber and EPA+DHA. The carbohydrate source is maltodextrin which is a simple sugar and in the current dose might be disadvantageous regarding late gastric dumping. Furthermore the product is not highly concentrated. A dosage of about 200 ml is required to supply the patient with 20 g protein. It is of crucial importance for post bariatric surgery that the nutrients can be offered in a small volume of 150 ml, preferably 125 ml.

SUMMARY OF THE INVENTION

The objective of the invention is therefore to prepare a balanced liquid nutritional product that addresses the specific nutritional needs of bariatric surgery patients. Compositions according to the invention are specifically designed for use in bariatric surgery patients (a1) for inducing liver size reduction when used pre-operatively, (a2) for controlling inflammation, (a3) for preventing dumping-syndrome when used post-operatively, (a4) for induction of weight loss and more specific fat mass pre and post surgery, (b1) for treatment of post-operative nutritional deficiencies, (b2) to maintain nitrogen equilibrium to prevent loss of muscle mass and/or muscle function, (b3) for improvement of post-meal glucose response by avoiding high glucose and with that high insulin peaks, (b4) prevention and improving GI function or bowel health, (b5) for prevention and/or treatment of bone calcium depletion and osteopenia, and (c1) for inducing moderate satiety. The product is therefore designed for both pre and post operative bariatric surgery patients, to be taken as part of a prescribed diet plan.

The composition according to the invention will be a ready-to-use high protein liquid nutritional product (which may be hypocaloric) and will include dietary fibre and a specially designed blend of vitamins and minerals. The product will allow patients to consume large amounts of essential nutrients in small portions. The product preferably will be close to (or possibly meet or exceed) RDIs for most micronutrients except e.g. for magnesium and vitamin A, and may contain specifically increased levels of some minerals, trace elements and vitamins. The product may meet or exceed RDIs for all micronutrients.

According to the present invention there is provided liquid composition having an energy content between 80-160 kcal/100 ml, a protein content between 40-80 En %, a digestible carbohydrate content between 0-30 En %, preferably less than 2, a fat content between 5-40 En %, a soluble dietary fibre content between 1.5-8 g/100 kcal, and micronutrients, wherein the micronutrients comprise calcium in an amount between 150-1000 mg/100 kcal, phosphorus in an amount between 100-1000 mg/100 kcal, with a Ca:P ratio of at least 1.0, iron in an amount between 4-50 mg/100 kcal, vitamin D in an amount between 2-400 mcg/100 kcal and vitamin B12 in an amount between 0.5-300 mcg/100 kcal.

In the above definition the term "En %" is the percentage of energy delivered by the component in relation to the total energy content of the composition excluding possible calories from the indigestible carbohydrates. Preferred features of the composition are set out as (i)-(ix) below.
(i) The protein source is milk based.
(ii) The carbohydrates induce a moderate to low glycemic response and/or do not induce side effects of late gastric dumping.
(iii) The fat is a blend of oils of plant origin to provide an optimal ratio of linoleic to α-linolenic acid. The ratio linoleic to α-linolenic acid is preferably between 3 and 6.
(iv) Eicosapentanoic acid (EPA) is present in an amount between 4 and 15 wt % based on total fatty acid content.
(v) The soluble dietary fibre preferably comprises galacto-oligosaccharides, inulin and/or oligo fructose. Even more preferably inulin and/or oligo fructose since the composition will than be lactose free. The presence of lactose is disadvantageous since some bariatric surgery patients lack sufficient activity of the enzyme lactase.

Preferred compositions in accordance with the invention comprise a combination of all of features (i)-(v) above together with the previously indicated amounts for phosphorus and calcium.

Further examples of preferred compositions in accordance with the invention have a digestible carbohydrate content between 10-30 En %, a fat content between 5-30 En % and an amount of iron of between 4-25 mg/100 kcal, and an amount of vitamin B12 of 0.5-150 mcg/100 kcal.

For certain embodiments of the invention, the digestible carbohydrate content may be 1.0-20 En %. Alternatively or additionally the vitamin B12 content may be 5-300 mcg/100 kcal.

DETAILED DESCRIPTION OF THE INVENTION

The product according to the invention is intended to be used to (i) support liver size reduction when used pre-operatively, (ii) to control inflammation post-surgery and (iii) to avoid dumping syndrome post-surgery, (iv) to maintain nitrogen levels and with that to prevent muscle loss and muscle function, (v) to induce weight loss and more specific fat mass pre and post surgery, and (vi) to prevent bone calcium depletion leading to osteopenia.

The composition according to the invention will be a neutral pH, highly concentrated, ready-to-consume, liquid nutritional product which fits in a hypocaloric high protein diet. The product addresses pre and post-operative nutritional deficiencies by aiding protein uptake, mineral absorption, improvement of GI function/bowel health and has a moderate satiety inducing effect and gives a low glycemic load.

Protein Source:

The protein content of the composition is 40-80 En %. The composition preferably provides 12-20 g protein per 100 kcal, more preferably 13-20 and even more preferably 14-20 g/100 kcal. The composition preferably provides 20-50 g protein in total per day, the remainder being provided from the diet. Daily requirements are 1.5 to 2.5 g/kg/d/IBW for bariatric patients. A low lactose or lactose free protein source is preferred due to the lactose intolerance experienced post surgery.

In a preferred embodiment the protein (i) has a high biological value, (ii) gives a sustained release of amino acids into the blood stream and (iii) is an excellent source of micronutrients, like calcium. In a preferred embodiment the protein source consists of intact, i.e. unhydrolysed protein. In another preferred embodiment the protein source is milk based, because milk protein has an outstanding amino acid composition. It is even more preferred if the protein consists for a large part of casein due to the high calcium and phosphorus content. The calcium in casein micelles has a very high bio-availability. In the stomach casein aggregates and this results in an increase of the viscosity of the stomach content. As a result relatively shortly after consumption a strong sense of fullness will be experienced by the patient. The stomach content will be released gradually and amino acids will be taken up into the blood stream. As a result a sustained release of amino acids into blood stream is observed. This prevents feelings of satiety from developing. Especially post surgery patients do not profit from high satiety inducing products, since those products limit their intake, which may lead to shortages of essential nutrients.

In another preferred embodiment the milk protein source can be a combination of intact caseinate and hydrolysed whey protein. Having a combination of casein and whey protein gives an even better amino acid composition. Furthermore whey protein is known as a fast protein having the advantage that amino acids become available for the patient relatively quickly.

Digestible Carbohydrate

According to the invention the product is designed to have a low calorie density. The amount of digestible carbohydrate in the composition is 0-30 En % and is intended to provide between 0-55 g digestible carbohydrates per day. It is particularly preferred that the composition is intended to provide between 0-10 g digestible carbohydrates per day, although in some instances amounts in the range 8-55 g digestible carbohydrates per day may be suitable. A preferred embodiment comprises between 0-25 g digestible carbohydrates per 100 kcal and even more preferred between 0.5 and 20 g per 100 kcal and most preferred between 0.5 and 5 g per 100 kcal. It is particularly preferred that the composition comprises less than 2 g digestible carbohydrates per 100 kcal.

An important consideration with gastric bypass patients is the possibility of dumping syndrome. Under normal conditions the stomach serves as a reservoir that releases food downstream only at a controlled rate, avoiding sudden large influxes of glucose. Dumping syndrome occurs with gastric bypass only and is divided into early and late phases. Early dumping syndrome happens when the lower end of the small intestine fills too quickly with undigested food from the stomach. It is due to the rapid-gastric emptying causing bowel distention plus movement of fluid from the blood to the intestine to dilute the intestinal contents. Patients can develop abdominal bloating, pain, vomiting and vasomotor symptoms (flushing, sweating, rapid heart rate, light headedness). Other patients may have diarrhea. These symptoms usually occur 30 to 60 minutes after eating. Late dumping syndrome is the mechanism by which glucose intake can create low blood sugar. The small bowel is very effective in absorbing glucose, so that the rapid absorption of a relatively small amount of glucose can cause the glucose level to rise rapidly. This leads to an increase of the insulin level. However, if the glucose that started the whole cycle was a small amount, the glucose level will fall back down at about the time the insulin surge starts. These factors combine to produce hypoglycemia (low blood sugar) which causes the individual to feel weak, sleepy and profoundly fatigued. In another preferred embodiment the amount and type of digestible carbohydrates is such that slow release of glucose into the bloodstream is ensured. This can be achieved by offering low amounts of digestible carbohydrates in combination with carbohydrates having a low and/or medium glycemic index. Examples of low or moderate glycemic index carbohydrate are: lactose, sucrose, fructose, trehalose, isomaltulose. Consumption of a low GI product has a positive effect on overall glycemic control in obese diabetic patients and in conjunction with weight loss will result in patients reducing or completely stopping their diabetic medications. Therefore, the compositions according to the invention are particularly suitable for improving the glycemic control of obese diabetic patients pre and post bariatric surgery, while at the same time weight loss associated nutritional deficiencies can be prevented or restored.

Since part of the carbohydrates are also needed for taste purposes and not for their nutritional purpose, in a preferred embodiment, part of the carbohydrates is replaced by low calorie artificial sweeteners such as e.g. aspartame, saccharine, cyclamate, etc.

Indigestible Carbohydrate

The composition contains soluble dietary fibre as indigestible carbohydrate. Preferably the levels of soluble dietary fibre will be between 1.5-8 g/100 kcal, preferably between 2-6 g/100 kcal, providing between 2.8-22.5 g indigestible carbohydrates per day.

Dietary fibre is edible matter that is not absorbed by the small intestine. When it passes through the large intestine, soluble fibre is fermented. It is understood to have a prebiotic effect (stimulate probiotic bacteria in the gut). By modification of the intestinal microflora, dietary fibre can have the following positive effects: promotion of good digestion, prevention of growth of harmful bacteria, stimulation of the immune system, and increase of the resistance to infection.

Dietary fibers as used in this invention are typically resistant to digestion and absorption in the human small intestine with preferably a complete or partial fermentation in the large intestine. Preferably the present composition comprises at least one dietary fibre capable of stimulating the growth of bifodobacteria in the gut selected from the group consisting of galactooligosaccharides including trans galactooligosaccharides, inulin, fructooligosaccharides, xylooligosaccharides, palatinoseoligosaccharide, resistant starch, lactulose, lactosucrose, mannanoligosaccharides, isomaltooligosaccharides, maltooligosaccharides, glucomannan, arabinogalactan, soybean oligosaccharide, gentiooligosaccharide, pectin, pectate, chondroitine, hyaluronic acids, heparine, heparane, bacterial carbohydrates, sialoglycans, fucooligosaccharides, xanthan gum, polydextrose (PDX), galactomannans, preferably guar gum, arabinoxylan, preferably MGN-3 Rice Bran Arabinoxylan according to U.S. Pat. No. 5,560,914, xyloglycan, callose, and/or degradation products thereof. All of these have beneficial prebiotic and bifidogenic effects in the intestinal system. PDX is a non-digestible carbohydrate that has been synthesized from randomly cross-linked glucose and sorbitol.

It is well reported that dietary fibres are important for development of good colonic microflora with stimulation of gastrointestinal health via increasing the body's natural resistance to invading pathogens. Therefore a preferred use of the compositions according to the present invention, comprising dietary fibres, are particularly useful in stimulating the natural resistance to invading pathogens in obese bariatric surgery patients. A preferred embodiment according to the invention comprises a combination of FOS in combination with AOS and/or low viscosity pectin. The combination may also include GOS.

Increased blood cholesterol is a major problem in obese bariatric surgery patients. Part of the dietary treatment of these patients is related to the lowering of the blood cholesterol levels. A primary benefit of including dietary fibre is its effect on lowering blood cholesterol levels which has been demonstrated by several studies [4;5].

Another benefit of dietary fibers is their ability to increase mineral absorption, particularly calcium. The inventors found that this benefit is especially desirable in obese individuals who are more at risk of suffering osteoarthritis, osteoporosis and weak bones in later life and in patients following GBP surgery who may be at risk of bone demineralization due to vitamin D and calcium deficiencies.

One of the proposed benefits of the product for patients following gastric bypass surgery is inclusion of non-nutritive ingredients that induce feelings of satiation and satiety and thus prevent a patient consuming a larger portion of food than required.

Furthermore inclusion of dietary fibre can have a glycemic index lowering effect by decreasing the rate of gastric emptying, which is positive for obese patients with diabetes.

Fat:

The present liquid enteral nutritional composition further comprises fat. The consumption of fats is discouraged in this patient group as they can significantly increase the calorie content of the diet. The aim is to produce a supplement that is low in calories with fat levels that are between 5-30 En %. Fat is sometimes required to optimise taste and acceptability of the product. It also can include components with a specific health effect.

The fat may either be an animal fat or a vegetable fat or both. Although animal fats such as lard or butter have essentially equal caloric and nutritional values and can be used interchangeably, vegetable oils are highly preferred in the practice of the present invention due to their readily availability, ease of formulation, absence of cholesterol and lower concentration of saturated fatty acids. Fat sources to be used comprise corn oil, sunflower oil, safflower oil, canola oil, coconut oil and/or soybean oil or combinations thereof. In one embodiment the fat blend will provide an optimal ratio of linoleic (LA) to a-linolenic acid (ALA). Preferably the level of LA provided is between 0.15-0.70 g/100 kcal. Preferably the level of ALA provided is between 0.05-0.25 g/100 kcal.

The fat may include medium chain triglycerides (MCT, mainly 8 to 10 carbon atoms long), long chain triglycerides (LCT) or any combination of the two types. MCTs are beneficial because they are easily absorbed and metabolized in a metabolically-stressed patient. Moreover, the use of MCTs will reduce the risk of nutrient malabsorption. LCT sources, such as canola oil, rapeseed oil, or corn oil are preferred because they can reduce immune suppression associated with certain types of fatty acids concentrated in the body.

Preferably, the fat comprises 10 to 60 weight % (e.g. 30 to 60 weight %) of animal or algal fat, 40 to 70 weight % of vegetable fat and 0 to 20 weight % of MCTs based on total fat of the composition. The animal fat preferably comprises a low amount of milk fat, i.e. lower than 6 weight %, especially lower than 3 weight % based on total fat. In particular, a mixture of corn oil, egg oil, and/or canola oil and specific amounts of marine oil may be used. Egg oils, fish oils and algal oils are a preferred source of non-vegetable fats.

For increased anti-inflammatory effect the fat blend preferably comprises eicosapentanoic acid and docosahexanoic acid. Marine oils containing DHA are preferably present in the composition according to the invention in an amount lower than 25 weight %, preferably lower than 15 weight % based on total fat. On the other hand, inclusion of eicosapentanoic acid (EPA) is highly desirable for obtaining the maximum health effect. The amount of EPA ranges preferably between 4 weight % and 15 weight %, more preferably between 8 weight % and 13 weight % based on total. The weight ratio EPA:DHA is advantageously at least 6:4, for example between 2:1 and 10:1.

Especially for liquid compositions that are to be consumed orally, in order to prevent formation of off-flavours and to decrease a fishy after-taste, it is recommended to select ingredients that are relatively low in docosahexanoic acid (DHA), i.e. less than 6 weight %, preferably less than 4 weight % based on total fat.

Also, the liquid nutritional composition according to the invention may beneficially comprise an emulsifier. Commonly known emulsifiers may be used and generally the emulsifier contributes to the energy content of the fat in said composition.

Micronutrients:

The composition preferably contains increased levels of all micronutrients, and preferably of calcium, phosphorus, iron, vitamin $B_{12}$, vitamin C and fat soluble vitamins (vit D, E, K) to meet specific requirements of patients following bariatric surgery. Levels may differ depending on the type of surgery. After RYGBP, VBG and BPD the need for micronutrient supplementation is larger than after AGB. The rationale for these is described in detail below. The remainder of the micronutrients (vitamins, trace elements and optionally magnesium) will be provided at levels that will meet RDAs between 100-200%, as it is suggested in clinical practice that all patients take a prenatal multivitamin supplement (containing increased iron and other micronutrients) as a prophylactic measure regardless of whether they have identified deficiencies or not. The levels of the electrolytes sodium, potassium and chloride will be at levels inherent in the ingredients used.

Calcium, Vitamin D and Phosphorus:

Abnormal levels of calcium and vitamin D have been reported pre-surgery. It is postulated that this is possibly due to reduced exercise, decreased sunlight exposure and increased storage in body fat with resultant decreased bioavailability.

Calcium deficiency is predictable in gastric bypass patients as calcium in food is mostly absorbed in the duodenum and proximal jejunum, which is bypassed in RYGBP, via an inactive, saturable process mediated by Vitamin D. Stomach acid is also required to convert calcium in food to a soluble form for absorption. Decreased intakes of dairy products due to intolerance, secondary to lactase deficiency or previously masked intolerance will also lead to reduced calcium intakes post surgery.

Levels of calcium in the product according to the invention are 150-1000 mg/100 kcal, more preferably 200-750 mg/100 kcal, more preferably 250 mg/100 kcal. To increase bioavailability, calcium in the form of casein-bound calcium will be used. In another embodiment to increase calcium uptake dietary fiber will be included.

Several retrospective studies have shown a deficiency of vitamin D following gastric bypass surgery. Calcium can also be absorbed in the alkaline environment of the small intestine through a vitamin D dependent mechanism. The preferred range of vitamin D per 100 kcal is between 2-400 mcg, preferably between 4-40 mcg per 100 kcal. In a preferred embodiment vitamin $D_3$ is used since this form is more effective than $D_2$ at increasing levels of vitamin D hormone in circulation. These higher levels help to optimise calcium absorption.

In order to maximise bone health it is prudent to maintain a Ca:P ratio of at least 1.0. Thus the proposed levels of phosphorus will be 100 mg-1000 mg per 100 kcal, preferably between 100-750 mg per 100 kcal.

Iron:

Iron deficiency appears to be quite common following bariatric surgery (RYGBP, VBG and BPD). Incidences of deficiency ranging from 14-52% have been reported. In order to be absorbed dietary non-haem iron, requires gastric acid to reduce the ferric ion to the ferrous state. After gastric bypass, the amount of gastric acid is greatly reduced thereby limiting absorption of iron from food. Iron is also absorbed in the duodenum (which is totally bypassed) and proximal jejunum (some of which is bypassed in the surgery). In menstruating women this deficiency is further exacerbated. The composition comprises 4 mg to 50 mg iron per 100 kcal, preferably between 15-50 mcg/100 kcal, although for some embodiments of the invention the range may be between 4-15 mcg/100 kcal.

Vitamin B12:

In normal, healthy individuals, gastric acid and peptic acid are required to release vitamin B12 from food. In the duodenum, the vitamin then binds to intrinsic factor, which is then absorbed in the terminal ileum. Post gastric bypass bariatric surgery, gastric acid is virtually absent as the acid secreting cells are mostly located in the fundus of the stomach, which is bypassed, making it difficult for patients to effectively release Vitamin $B_{12}$ bound in food. Good sources of this vitamin are primarily red meats and dairy products that may be excluded or limited from the diets of this patient group due to intolerances, making it even more difficult to meet requirements. It has been described in literature that there is frequently a lack of symptoms which may lead to delayed diagnosis of a condition which results in irreversible neurological damage if deficiency is maintained for a long period of time.

Since gastric bypass patients have problems with vitamin B12 absorption it is preferred to go for higher levels of this vitamin in order to maximise availability of the vitamin as total absorption increases with increasing intake. The composition preferably comprises between 50 to 250 mcg vitamin B12 per 100 kcal, preferably vitamin B12 between 100-200 mcg per 100 kcal.

Vitamin C and vitamin E:

Preferred vitamin C levels are between 40-2000 mg (e.g. 50-2000 mg) per 100 kcal product. Preferably the daily dose of vitamin C provided by the formulation is between 50 and 150 mg or even more preferably between 60 and 100 mg.

Preferred levels of vitamin E are between 10-1000 mg (e.g. 20-1000 mg) tocopherol equivalents per 100 kcal. Preferably, this will provide a total daily intake of at least 40 mg.

These increased levels of vitamin C & E are incorporated due to increased iron intakes in this product. The aim is to provide levels that at least meet recommended intakes and will also act to reduce oxidative stress.

Due to bariatric surgery fat uptake and digestion may be disturbed. As a result uptake of fat soluble vitamins may be insufficient. It is therefore preferred to for higher levels to maximise availability. A preferred composition comprises between 150-1000 mcg vitamin A or beta carotene (vit A precursor) per 100 kcal, preferably vitamin A or beta carotene is between 200-750 mcg per 100 kcal. The composition preferably comprises between 3.5 to 200 mcg vitamin K per 100 kcal, preferably vitamin K between 3.5-100 (more preferably 5-100) mcg per 100 kcal or even more preferably between 3.5-20 mcg/100 kcal, most preferably between 5-10 mcg/100 kcal.

Energy Density:

Total calories have been kept to a minimum. Preferably a single dose contains less than 250 kcal, even more preferably between 80 and 200 kcal. In one embodiment daily consumption will be less than 4 dosages per day, more preferably 1-2 dosages per day.

Viscosity

In one embodiment the invention is a liquid nutritional product suitable to be drunk and thus has a viscosity below 150 mPa·s, preferably below 100 mPa·s, more preferably below 80 mPa·s, even more preferably below 70 mPa·s. The viscosity is determined in a rotational rheometer using a cone-plate geometry at 20° C. at a shear rate of 50 1/s. In another embodiment the invention is a texturised product ready for consumption to be eaten with a spoon and thus having a viscosity of at least 350 mPa·s, preferably above 750 mPa·s, more preferably between 1000 and 4000 mPa·s.

Packaging

Since bariatric surgery patients have a small stomach volume, it is essential that the volume is kept low. Preferably the volume of a single dose should not exceed 150 ml per dose, more preferably no more than 125 ml and even more preferably less than 100 ml. The inventors expect that if the volume would exceed the maximum volume of 150 ml, the bariatric surgery patients will not be able to comply with the product intake required for obtaining the claimed effects of the product.

Uses of the Compositions

Morbidly obese patients suffer from several more or less severe symptoms as there are: diabetes, hyperlipidemia, hypertension, and obstructive sleep apnea. It is reported that bariatric surgery induced weight loss gives improvement or even complete resolution of these symptoms [7]. It is an object of the present invention to provide a method and a composition to improve several symptoms in bariatric surgery patients. Examples of the symptoms are inability to have sufficient food intake, inability to have sufficient protein intake, inability to have sufficient micronutrient intake, symptoms coming from high product osmolarity (incl early gastric dumping), symptoms caused by high glucose and insulin peaks (incl late gastric dumping), coronary heart disease, unhealthy gut, loss of nitrogen, loss of muscle mass, calcium deficiency, osteopenia, iron deficiency, inflammation. The product of the invention can also be used to treat the above-described symptoms in obese pre- and post-surgery patients, for example to achieve liver-size reduction, in malnourished obese, and to maintain and/or increase muscle mass.

Osteopenia refers to bone mineral density (BMD) that is lower than normal peak BMD but not low enough to be classified as osteoporosis. Bone mineral density is a measurement of the level of minerals in the bones, which indicates how dense and strong they are. If your BMD is low compared to normal peak BMD, you are said to have osteopenia. Having osteopenia means there is a greater risk that, as time passes, you may develop BMD that is very low compared to normal, known as osteoporosis. Patients that are obese and undergo bariatric surgery are at increased risk to develop Osteopenia and osteoporosis. The compositions according to the invention are particularly suitable to prevent and/or treat osteopenia and osteoporosis in these patients because they comprise relatively high amounts of calcium, phosphorus and vitamin D.

Dumping syndrome is most common in patients with certain types of stomach surgery, such as a gastrectomy or gastric bypass surgery that allow the stomach to empty rapidly. Gastric dumping syndrome, or rapid gastric emptying, happens when the lower end of the small intestine, the jejunum, fills too quickly with undigested food from the stomach. "Early" dumping begins during or right after a meal. Symptoms of early dumping include nausea, vomiting, bloating, cramping, diarrhea, dizziness and fatigue. "Late" dumping happens 1 to 3 hours after eating. Symptoms of late dumping include weakness, sweating, and dizziness. Many people have both types. In addition, people with this syndrome often suffer from low blood sugar, or hypoglycemia, because the rapid "dumping" of food triggers the pancreas to release excessive amounts of insulin into the bloodstream. This type of hypoglycemia is referred to as "alimentary hypoglycemia". The compositions according to the invention are particularly suitable for the treatment and/or prevention of dumping syndrome since the high protein levels and fibers in the product will decrease the rate of gastric emptying and the low glycemic carbohydrates will decrease the raise in glucose levels, i.e. the rate of absorption of glucose in the blood.

Obesity is the main reason for performing bariatric surgery. Before the start of the operation it may be needed to induce weight loss and after a successful operation it may be necessary to induce satiety in combination with the provision of sufficient essential vitamins and minerals. In a preferred embodiment, the composition according to the invention can be used for the treatment of weight loss-related symptoms in bariatric surgery patients.

Chronic microinflammation or 'low grade inflammation' plays an important role in cardiovascular morbidity in obese subjects. The presence of significant amounts of ALA and/or EPA/DHA in the fat blend of the composition of the present invention decreases microinflammation in the target group of morbidly obese patients. Therefore the composition according to the invention may preferably be used for the treatment and/or prevention of chronic microinflammation in obese patients.

The following compositions according to the invention have been prepared (Table 1). The compositions are produced in a manner known per se, e.g. by mixing the ingredients, without difficulties, are shelf-stable, have desirable organoleptic properties, have a very high nutrient density and are effective for a person in need thereof.

TABLE 1

| | Amount per 100 ml of product | | | |
|---|---|---|---|---|
| Component | A1 | A2 | A3 | A4 |
| Energy (kcal/100 ml) | 120 | 108 | 120 | 120 |
| Protein (En %) | 53.3 | 53.3 | 53.3 | 72 |
| Protein (g) | 16.0 | 13.3 | 16.0 | 16.0 |
| Casein (wt % protein) | >95 | >95 | 45 | >95 |
| Whey (wt % protein) | <5 | <5 | 55** | >5 |
| Fat (En %) | 18 | 18 | 18 | 25 |
| Fat (g) | 2.40 | 2.14 | 2.40 | 2.40 |
| LA (g) | 1.25 | 1.05 | 1.25 | 1.25 |
| ALA (g) | 0.33 | 0.28 | 0.33 | 0.33 |
| EPA + DHA (g) | 0.20 | 0.17 | 0.20 | 0.20 |
| Carbohydrates (En %) | 29.0 | 29.0 | 29.0 | 2.90 |
| Carbohydrates (g) | 8.6 | 7.8 | 8.6 | 0.86 |
| Lactose (g) | 1.4 | 1.3 | 1.3 | 0.1 |
| Sucrose (g) | 4.9 | 4.4 | 4.7 | 0 |
| Maltodextrin (DE 19) (g) | 2.3 | 2.1 | 2.3 | 0 |
| Isomaltulose (g) | | | 0.3 | |
| Sucralose (g) | | | | 0.03 |
| Dietary fiber (g) | 3.60 | 3.2 | 3.6 | 5 |
| GOS (g) | 3.25 | 2.9 | 2.7 | |
| FOS/inulin (g) | 0.35 | 0.3 | 0.3 | 5 |
| Low visc pectin (g) | | | 0.6 | |
| Minerals | | | | |
| Calcium (mg) | 345 | 310 | 345 | 345 |
| Phosphorus (mg) | 295 | 262 | 225 | 295 |
| Iron (mg) | 6 | 12 | 16 | 30 |
| Vitamins | | | | |
| Vitamin B12 (mcg) | 1.26 | 1.05 | 126 | 157 |
| Vitamin D (mcg RE) | 4.2 | 3.5 | 4.2 | 20 |
| Unit dosage (ml) | 125 | 150 | 125 | 125 |

*excl dietary fiber (4 kcal/g)
**Hydrolysed whey protein

REFERENCES

1. Xanthakos S A, Inge T H. Nutritional consequences of bariatric surgery. Curr Opin Clin Nutr Metab Care 2006; 9:489-96.
2. Malinowski S S. Nutritional and metabolic complications of bariatric surgery. Am J Med Sci 2006; 331:219-25.
3. Parkes E. Nutritional management of patients after bariatric surgery. Am J Med Sci 2006; 331:207-13.
4. Jackson K G, Taylor G R, Clohessy A M, Williams C M. The effect of the daily intake of inulin on fasting lipid, insulin and glucose concentrations in middle-aged men and women. Br J Nutr 1999; 82:23-30.
5. Brighenti F, Casiraghi M C, Canzi E, Ferrari A. Effect of consumption of a ready-to-eat breakfast cereal containing inulin on the intestinal milieu and blood lipids in healthy male volunteers. Eur J Clin Nutr 1999; 53:726-33.
6. Cook J D, Monsen E R. Vitamin C, the common cold, and iron absorption. Am J Clin Nutr 1977; 30:235-41.
7. Buchwald H. et al. Bariatric surgery: A systematic review and analysis. JAMA Ocotber 13, 2004-Vol 292, No 14.

The invention claimed is:

1. A liquid composition comprising having an energy content between 80-160 kcal/100 ml, a protein content between 14-20 g protein per 100 kcal, a digestible carbohydrate content between 0-30 En %, a fat content between 5-40 En %, the fat comprising a blend of eicosapentanoic acid and docosahexanoic acid, a soluble dietary fiber content between 1.5-8 g/100 kcal, and micronutrients, wherein the micronutrients comprise calcium in an amount between 150-1000 mg/100 kcal, phosphorus in an amount between 100-1000 mg/100 kcal, with a Ca:P ratio of at least 1.0, iron in an amount between 4-50 mg/100 kcal, vitamin D in an amount between 2-400 mcg/100 kcal and vitamin B12 in an amount between 0.5-300 mcg/100 kcal.

2. The composition according to claim 1 which comprises a digestible carbohydrate content between 10-30 En %.

3. The composition according to claim 1 which comprises a fat content between 5-30 En %.

4. The composition according to claim 1 which comprises iron in amount between 4-25 mg/100 kcal.

5. The composition according to claim 1 which comprises vitamin B12 in an amount between 0.5-150 mcg/100 kcal.

6. The composition according to claim 1 which comprises a digestible carbohydrate content between 10-30 En %, a fat content between 5-30 En %, an iron in an amount between 4-25 mg/100 kcal, and vitamin B12 in an amount between 0.5-150 mcg.

7. The composition according to claim 1 which comprises vitamin B12 in an amount between 5-300 mcg/100 kcal.

8. The composition according to claim 1 which comprises a digestible carbohydrate content between 1.0-20 En %.

9. The composition according to claim 1 which comprises less than 2 g digestible carbohydrates per 100 kcal.

10. The composition according to claim 1 wherein the digestible carbohydrate is a low glycemic carbohydrate selected from the group consisting of fructose, galactose, isomaltulose, slow digestible starch and combinations thereof.

11. The composition according to claim 1 wherein the protein is unhydrolysed protein.

12. The composition according to claim 1 wherein the protein is a low lactose or lactose free, protein source.

13. The composition according to claim 1 comprising 2-10 g, preferably 2-6 g soluble dietary fiber per 100 kcal.

14. The composition according to claim 1 wherein the soluble dietary fibers comprise inulin and/or oligo fructose.

15. The composition according to claim 1 wherein the fat provides 0.15-0.70 g of linoleic acid per 100 kcal.

16. The composition to claim 1 wherein the fat provides 0.05-0.25 g α-linolenic acid per 100 kcal.

17. The composition according to claim 1 wherein the weight ratio of eicosapentanoic acid to docosahexanoic acid is at least 6:4.

18. The composition according to claim 17 wherein said ratio is from 2:1 to 10:1.

19. The composition according to claim 1 comprising 200-750 mg calcium per 100 kcal.

20. The composition according to claim 1 comprising 4 to 50 mg iron per 100 kcal.

21. The composition according to claim 1 comprising 4 to 40 mcg vitamin D per 100 kcal.

22. The composition according to claim 1 wherein the vitamin D consists essentially of vitamin D3.

23. The composition according to claim 1 comprising 0.75 to 250 mcg vitamin B12 per 100 kcal.

24. The composition according to claim 1 for
   a. prevention and/or treatment of bone calcium depletion and osteopenia,
   b. prevention and treatment of post-operative nutritional deficiencies,
   c. induction of weight loss pre and post surgery, or
   d. maintain glycaemic control in obese bariatric surgery patients.

25. A method for
   a. prevention and treatment of post-operative nutritional deficiencies, or
   b. induction of weight loss pre and post surgery in obese gastric bypass patients, wherein the method comprises the administration of a composition according to claim 1.

* * * * *